(12) United States Patent
Yamada et al.

(10) Patent No.: US 7,754,497 B2
(45) Date of Patent: Jul. 13, 2010

(54) METHOD FOR IMMOBILIZING PROTEINS

(75) Inventors: Tsuyoshi Yamada, Osaka (JP); Yorimasa Suwa, Chiba (JP); Takeshi Tsutsumi, Osaka (JP)

(73) Assignee: Reverse Proteomics Research Institute Co., Ltd., Kisarazu-shi (JP)

( * ) Notice: Subject to any disclaimer, the term of this patent is extended or adjusted under 35 U.S.C. 154(b) by 683 days.

(21) Appl. No.: 10/569,883

(22) PCT Filed: Aug. 24, 2004

(86) PCT No.: PCT/JP2004/012447

§ 371 (c)(1),
(2), (4) Date: Feb. 28, 2006

(87) PCT Pub. No.: WO2005/022156

PCT Pub. Date: Mar. 10, 2005

(65) Prior Publication Data

US 2009/0098568 A1    Apr. 16, 2009

(30) Foreign Application Priority Data

Aug. 29, 2003 (JP) ............................. 2003-307588

(51) Int. Cl.
*G01N 33/543* (2006.01)
(52) U.S. Cl. .................. 436/518; 435/7.1; 435/69.7; 435/174; 436/174; 436/178
(58) Field of Classification Search .............. 435/287.2, 435/6; 436/518; 422/102, 70, 100
See application file for complete search history.

(56) References Cited

U.S. PATENT DOCUMENTS

| | | | |
|---|---|---|---|
| 5,986,066 A * | 11/1999 | Barner et al. ............ | 530/391.1 |
| 6,642,014 B1 | 11/2003 | Pedersen et al. | |
| 6,688,181 B1 | 2/2004 | Clerc et al. | |
| 6,800,453 B2 * | 10/2004 | Labaer et al. ............ | 435/68.1 |
| 2002/0019009 A1 * | 2/2002 | Roggen et al. ............ | 435/7.1 |
| 2002/0049152 A1 * | 4/2002 | Nock et al. ............ | 514/2 |
| 2002/0076739 A1 * | 6/2002 | Aebersold et al. ......... | 435/7.92 |
| 2002/0106702 A1 * | 8/2002 | Wagner et al. ............ | 435/7.9 |
| 2002/0110932 A1 * | 8/2002 | Wagner et al. ............ | 436/518 |
| 2005/0048570 A1 | 3/2005 | Weber et al. | |

FOREIGN PATENT DOCUMENTS

| | | |
|---|---|---|
| JP | 10-512140 A | 11/1998 |
| JP | 2001-505764 A | 5/2001 |
| JP | 2002-523059 A | 7/2002 |
| JP | 2005-524829 A | 8/2005 |
| WO | WO-96/20403 A1 | 7/1996 |
| WO | WO-98/20343 A2 | 5/1998 |
| WO | WO-00/11211 A1 | 3/2000 |
| WO | WO-02/33044 A2 | 4/2002 |
| WO | WO-2004/046724 A1 | 6/2004 |

OTHER PUBLICATIONS

Office Action issued Jun. 2, 2009 in corresponding Japanese application No. 2004-553327.

* cited by examiner

*Primary Examiner*—Nelson Yang
(74) *Attorney, Agent, or Firm*—Birch, Stewart, Kolasch & Birch, LLP

(57) ABSTRACT

This invention provides a method for immobilizing proteins comprising: step 1 of purifying target proteins to be immobilized, which have a first tag portion and a second tag portion, with the use of the first tag portion; step 2 of activating reactive groups capable of covalently binding to the proteins on a carrier for immobilization; and step 3 of allowing a solution containing the proteins purified in step 1 to react with the carrier after step 2, wherein, in step 3, the proteins are immobilized on the carrier via interactions between the second tag portion and the site of the carrier to which the second tag portion binds and via covalent binding between the reactive groups and the proteins. This method enables the stable immobilization of various types of target proteins on a carrier regardless of the amounts of target proteins and without non-specific immobilization of contaminating proteins.

11 Claims, 9 Drawing Sheets

A: Apply
E: Eluate

```
SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: His-tag including a termination codon

<400> SEQUENCE: 1
catcaccatc accatcacta a                                              21

<210> SEQ ID NO 2
<211> LENGTH: 6
<212> TYPE: PRT
<213> ORGANISM: Artificial Sequence
<220> FEATURE:
<223> OTHER INFORMATION: His-tag

<400> SEQUENCE: 2

His His His His His His
  1               5

<210> SEQ ID NO 3
<211> LENGTH: 45
<212> TYPE: DNA
<213> ORGANISM: Artificial Sequence
<220> FEATURE:
<223> OTHER INFORMATION: His-tag and FLAG-tag including an initiation
      codon

<400> SEQUENCE: 3
atgcatcacc atcaccatca cgactacaag gacgacgatg acaaa                    45

<210> SEQ ID NO 4
<211> LENGTH: 15
<212> TYPE: PRT
<213> ORGANISM: Artificial Sequence
<220> FEATURE:
<223> OTHER INFORMATION: His-tag and FLAG-tag including an initiation
      codon

<400> SEQUENCE: 4

Met His His His His His His Asp Tyr Lys Asp Asp Asp Lys
  1               5                  10                  15
```

METHOD FOR IMMOBILIZING PROTEINS

TECHNICAL FIELD

The present invention relates to, for example, a method for immobilizing proteins that can be extensively utilized when immobilizing proteins on the surface of a carrier.

BACKGROUND ART

Information concerning protein-protein interactions and protein-compound interactions is very useful in discovering novel drug targets and/or novel candidate compounds for pharmaceutical preparations. Through a comprehensive analysis of protein functions, protein functions can be analyzed with the use of proteins expressed on a minute scale. This is important in terms of cost and throughput. In order to attain the aforementioned information or to implement protein function analysis with the use of proteins expressed on a minute scale, apparatuses that analyze interactions in real time based on the principle of surface plasmon resonance (SPR) without the use of a radioisotope, such as the Biacore 3000 (Biacore), have been used in recent years.

In such SPR-based interaction analysis, either the proteins or compounds to be analyzed are immobilized on a sensor chip, other proteins or compounds are allowed to react on the sensor chip, and changes in masses resulting from protein-protein or protein-compound interactions are detected as an SPR signal. Since this SPR-based interaction analysis is a technique for highly sensitive function analysis, the amount of proteins required therefor is advantageously small.

In SPR-based interaction analysis, for example, a method wherein amino groups of proteins are allowed to couple to carboxyl groups on a sensor chip under conditions of low pH and low salt concentration (i.e., amine coupling) is used when immobilizing proteins on the sensor chip. Under such conditions, however, proteins are likely to be deactivated, and acidic proteins cannot be immobilized. When a tag such as a histidine tag is used, a wide variety of histidine tag fusion proteins can be immobilized on the sensor chip. Such immobilization is unstable, and interaction analysis is impossible. In order to overcome such drawbacks, therefore, the present inventors continuously conducted tag-mediated binding and amine coupling of tag fusion proteins, developed a technique whereby almost all types of proteins could be stably immobilized on a sensor chip at physiological pH and physiological salt levels (affinity amine coupling), and already filed for a patent with regard to the same (JP Patent Application No. 2002-335334).

Protein expression systems that can express proteins regardless of species have been developed (e.g., a wheat germ cell-free system). In such expression systems, however, the expression levels of the target proteins are often very low. When small amounts of target proteins are immobilized on a sensor chip via the aforementioned affinity amine coupling technique, contaminating proteins are simultaneously coupled. This often yields unsatisfactory results in terms of an S/N ratio in the interaction assay.

DISCLOSURE OF THE INVENTION

Given the above circumstances, the present invention is directed to providing a method for stably immobilizing various types of target proteins on a carrier regardless of the amounts of the target proteins and without nonspecifically immobilizing contaminating proteins.

The present inventors have conducted concentrated studies in order to attain the above object and consequently discovered the following. When proteins having first tag portions and second tag portions are purified with the first tag portions and the purified proteins are immobilized on a carrier, the proteins are allowed to react with the carrier for immobilization after reactive groups on the carrier have been activated. This enables the second tag portions of the proteins to interact with and covalently bind to the carrier. Also, various types of target proteins can be stably immobilized on the carrier regardless of the amounts of the target proteins and without nonspecifically immobilizing contaminating proteins. Such discovery has led to the completion of the present invention.

The present invention includes the following.

(1) A method for immobilizing proteins comprising: step 1 of purifying target proteins to be immobilized, which have a first tag portion and a second tag portion, with the use of the first tag portion; step 2 of activating reactive groups capable of covalently binding to the proteins on a carrier for immobilization; and step 3 of allowing a solution containing the proteins purified in step 1 to react with the carrier after step 2, wherein, in step 3, the proteins are immobilized on the carrier via interactions between the second tag portion and the site of the carrier to which the second tag portion binds and via covalent binding between the reactive groups and the proteins.

(2) The method for immobilizing proteins according to (1), wherein step 1 comprises a step of separating and extracting the proteins via a purification means having the site to which the first tag portion binds.

(3) The method for immobilizing proteins according to (2), wherein the site to which the first tag portion binds is an antibody that reacts with the first tag portion.

(4) The method for immobilizing proteins according to (3), wherein the first tag portion is a FLAG tag, and the site to which the first tag portion binds is an anti-FLAG tag antibody.

(5) The method for immobilizing proteins according to (1), wherein the reactive groups are carboxyl groups and step 3 comprises subjecting the carboxyl groups to amine coupling with amino groups of the target proteins to be immobilized.

(6) The method for immobilizing proteins according to (1), wherein the second tag portion is a histidine tag, and step 3 comprises subjecting the histidine tag to interaction with the carrier.

(7) The method for immobilizing proteins according to (6), wherein step 3 comprises subjecting the histidine tag to a chelate-mediated interaction with the carrier.

(8) The method for immobilizing proteins according to (7), wherein step 3 comprises subjecting the histidine tag to an $Ni^{2+}$-nitrilotriacetic acid (Ni-NTA)-mediated interaction with the carrier.

(9) The method for immobilizing proteins according to (7), wherein step 3 comprises subjecting the histidine tag to an $Ni^{2+}$-iminodiacetic acid (Ni-IDA)-mediated interaction with the carrier.

(10) The method for immobilizing proteins according to (1), wherein the site of the carrier to which the second tag portion binds is an antibody that reacts with the second tag portion.

(11) The method for immobilizing proteins according to (10), wherein the second tag portion is a histidine tag, the antibody is an anti-histidine tag antibody, and step 3 comprises subjecting the histidine tag to the anti-histidine tag antibody-mediated interaction with the carrier.

(12) A method for detecting the protein-analyte affinity comprising a step of allowing a sample containing a target analyte to be detected to react with the carrier for immobilization having the proteins immobilized thereon via the method for immobilizing proteins according to any one of (1) to (11) and a step of detecting the affinity between the proteins immobilized on the carrier and the analyte contained in the sample.

(13) The method for detecting the protein-analyte affinity according to (12), wherein the step of detecting the affinity comprises detecting the affinity between the proteins and the analyte based on the principle of surface plasmon resonance.

(14) A carrier for immobilization having proteins immobilized thereon via the method for immobilizing proteins according to any one of (1) to (11).

(15) The carrier for immobilization having proteins immobilized thereon according to (14), which comprises a substrate, the polysaccharide molecule chain provided on the substrate and having reactive groups capable of covalent binding to the target proteins to be immobilized, which are introduced therein, and the target proteins to be immobilized, wherein the proteins are covalently bound to the reactive groups and interact with the polysaccharide molecule chain via a chelate.

Hereafter, the present invention is described in detail.

The method for immobilizing proteins according to the present invention can be employed when immobilizing proteins on a carrier for immobilization. This method is not restricted to a specific technical scope. For example, the method for immobilizing proteins according to the present invention can be employed when preparing a sensor chip having immobilized thereon proteins for analysis based on the principle of surface plasmon resonance (SPR). This method can also be utilized when preparing a sensor chip based on principles other than SPR. Examples of such principles other than SPR include the principle of quartz crystal microbalance (QCM) and that of dual polarization interferometry (DPI).

Further, the application of the method for immobilizing proteins according to the present invention is not limited to the preparation of sensor chips based on the principle of SPR or that of QCM. For example, the method of the present invention can be applied to the preparation of a so-called protein chip (a protein array) or an affinity bead (an affinity column).

Hereafter, a sensor chip used for SPR-based analysis is described by way of example. As shown in FIG. 1, this sensor chip comprises an optically transparent substrate 1, a metal membrane 2 provided on a principal surface of the substrate 1, and a carrier for immobilization 3 provided on the metal membrane 2. The carrier for immobilization 3 is prepared by immobilizing a self-assembled monolayer (SAM) having reactive groups such as carboxyl groups or an SAM and carboxymethyl dextran on the metal membrane 2.

The carrier for immobilization 3 comprises reactive groups that covalently bind to the target proteins to be immobilized. The reactive groups of the carrier for immobilization 3 refer to functional groups that covalently bind to the target proteins to be immobilized. Examples of reactive groups include carboxyl groups and thiol groups. The carrier for immobilization 3 may comprise a polysaccharide molecule chain into which reactive groups that covalently bind to the target proteins to be immobilized have been introduced. When the carrier for immobilization 3 comprises such a polysaccharide molecule chain, the target proteins to be immobilized covalently bind to reactive groups in the polysaccharide molecule chain, and the proteins form chelates with the polysaccharide molecule chain. Thus, the target proteins to be immobilized are immobilized on the carrier for immobilization 3. An example of such a polysaccharide molecule chain is dextran.

The carrier for immobilization 3 comprises the site to which the second tag portion of the target protein to be immobilized binds. Such site is adequately selected in accordance with the second tag portion. For example, such site may be nitrilotriacetic acid (NTA) or iminodiacetic acid (IDA) when the second tag portion is a histidine tag, it may be glutathione when the second tag portion is a glutathione S-transferase tag, and it may be maltose when the second tag portion is a maltose-binding protein tag. When the second tag portion is an antigenic peptide, the site of the carrier to which the second tag portion binds may be an antibody that undergoes an antigen-antibody reaction with the antigenic peptide.

In the method for immobilizing proteins according to the present invention, any protein can be immobilized without particular limitation, as long as such protein has 2 tag portions, i.e., the first and the second tag portions.

The first tag portion refers to a tag portion that is used when purifying the target proteins to be immobilized, which interacts with the site to which the first tag portion binds in the process of purification. The site to which the first tag portion binds is adequately selected in accordance with the first tag portion. For example, such site may be nitrilotriacetic acid (NTA) or iminodiacetic acid (IDA) when the first tag portion of the protein is a histidine tag, it may be glutathione when the first tag portion is a glutathione S-transferase tag, and it may be maltose when the first tag portion is a maltose-binding protein tag. When the first tag portion is an antigenic peptide, the site to which the first tag portion binds may be an antibody that undergoes an antigen-antibody reaction with the antigenic peptide. Examples of the first tag portion include a histidine tag (hereafter referred to as a "His tag"), a glutathione S-transferase tag (hereafter referred to as a "GST tag"), a maltose binding protein tag (hereafter referred to as an "MBP tag"), and an antigenic peptide tag. The "antigenic peptide tag" employs a peptide in which an antibody is present. Examples thereof include a His tag, a His G tag, an HA tag, a C-myc tag, a myc tag, a BPV-1 tag, a cl tag, a Cre recombinase tag, a FLAG tag, an NS1 (81) tag, a green fluorescent protein (GFP) tag, an IRS tag, a LexA tag, a Thioredoxin tag, a Polyoma virus medium T antigen epitope tag, an SV40 Large T Antigen tag, a Paramoxyvirus SV5 tag, a Xpress tag, a GST tag, and an MBP tag. A FLAG tag, an MBP tag, and a GST tag are particularly preferable as first tag portions.

The second tag portion interacts with the site of the carrier for immobilization 3 to which the second tag portion binds and plays a key role in the binding that takes place between proteins and the carrier for immobilization 3. Any site that differs from the first tag portion can serve as the second tag portion. Examples of the first tag portion listed above can be employed as the second tag portion. Particularly preferable examples of the second tag portion include a His tag and a GST tag.

Proteins having any characteristics or properties can be employed without limitation. For example, proteins may be basic or acidic, and they may be hydrophobic or hydrophilic.

A protein having a first tag portion and a second tag portion can be prepared using a recombinant vector comprising the first tag portion and the second tag portion in frame with a protein-encoding gene and allowing the expression of a fusion protein comprising the first tag portion, the second tag portion, and the protein. The first tag portion and the second tag portion of the fusion protein may be located on the N-terminal side or the C-terminal side of the protein, as long as they each independently function as a tag; i.e., as long as they can interact with the site to which the first or second tag portion binds. The first tag portion and the second tag portion of the fusion protein may be located adjacent to or separate from each other.

A target protein to be immobilized, which has a first tag portion and a second tag portion, can be prepared via any method without particular limitation. Examples of such method include: (1) a method wherein the protein-encoding gene is introduced into a vector, the resulting recombinant vector is introduced into a host cell, and the protein is then allowed to express in the host cell; and (2) a method wherein the protein is allowed to express in a cell-free system, such as a wheat germ cell-free system.

Examples of plasmid DNAs into which the genes encoding the target proteins to be immobilized, which have the first and the second tag portions, have been introduced that are employed in method (1) for preparing proteins include: *E. coli*-derived plasmids (e.g., pET-based plasmids such as pET30b, pBR-based plasmids such as pBR322 and pBR325, pUC-based plasmids such as pUC118, pUC119, pUC18, and pUC19, and pBluescript); *Bacillus sutbtilis*-derived plasmids (e.g., pUB110 and pTP5); and yeast-derived plasmids (e.g., YEp-based plasmids such as YEp13 and YCp-based plasmids such as YCp50). Examples of phage DNAs include λ phages (e.g., Charon 4A, Charon 21A, EMBL3, EMBL4, λgt10, λgt11, and λZAP). Further, vectors derived from animal viruses such as a retrovirus or a vaccinia virus, vectors derived from plant viruses such as cauliflower mosaic virus, or vectors derived from insect viruses such as a baculovirus can also be employed.

In order to insert genes encoding target proteins to be immobilized, which have a first tag portion and a second tag portion, into a vector, cDNAs of such genes are first cleaved with an adequate restriction enzyme, and the cleaved cDNAs are inserted into the restriction site or multicloning site of an adequate vector DNA to ligate the cDNAs to the vector. Alternatively, part of a vector and part of the cDNA of the gene may be provided with homologous regions to ligate them via an in vitro method using PCR or other means or via an in vivo method using yeast or the like.

Subsequently, a recombinant vector containing the gene encoding the target protein to be immobilized, which has the first tag portion and the second tag portion, is introduced into the host. Thus, a transformant that expresses the protein of interest can be obtained. The host is not particularly limited as long as the gene can be expressed therein. Examples of host include: plants of the Gramineae, Brassicaceae, Solanaceae, and Leguminosae; bacteria of *Escherichia* such as *Escherichia coli*, *Bacillus* such as *Bacillus subtilis*, or *Pseudomonas* such as *Pseudomonas putida*; yeast such as *Saccharomyces cerevisiae* and *Schizosaccharomyces pombe*; animal cells such as COS cells and CHO cells; and insect cells such as Sf9 cells.

The recombinant vector can be introduced into plants via conventional transformation techniques, such as electroporation, the *agrobacterium* method, the particle gun method, or the PEG method.

The recombinant vector can be introduced into bacteria via any method of introducing DNA into bacteria. Examples thereof include the calcium ion-based method and electroporation.

The recombinant vector can be introduced into yeast via any method of introducing DNA into yeast. Examples thereof include electroporation, the spheroplast method, and the lithium acetate method.

Examples of animal host cells include simian COS7 cells, Vero cells, Chinese hamster ovarian (CHO) cells, and murine L cells. The recombinant vector can be introduced into animal cells via any method of introducing DNA into animal cells. Examples thereof include electroporation, the calcium phosphate method, and lipofection.

An example of an insect host cell is the Sf9 insect cell. The recombinant vector can be introduced into insect cells via any method of introducing DNA into insect cells. Examples thereof include the calcium phosphate method, lipofection, and electroporation.

In method (2) for preparing proteins, Proteios (Toyobo Co., Ltd.) can be employed as the wheat germ cell-free system, for example. When Proteios (Toyobo Co., Ltd.) is employed, the mRNA is first synthesized in a reaction system that comprises, as a template, a recombinant vector for the wheat germ cell-free system (e.g., a pEU3-NII plasmid (Toyobo Co., Ltd.)) containing a gene encoding a target protein to be immobilized, which has a first tag portion and a second tag portion, and thermo T7 RNA polymerase (Toyobo Co., Ltd.). The synthesized mRNA is then subjected to protein removal via phenol/chloroform treatment and is then buffer-exchanged with the Proteios buffer via ethanol precipitation. In accordance with the protocol of Proteios, the target proteins to be immobilized, which have a first tag portion and a second tag portion, are synthesized using the synthesized mRNA.

In the method for immobilizing proteins according to the present invention, the target protein to be immobilized is first purified with the first tag portion. The term "purified with the first tag portion" refers to the interaction between the first tag portion of the target protein to be immobilized and the site to which the first tag portion binds, which is used to separate and extract the target protein to be immobilized from biological material containing contaminating proteins and the like. Examples of techniques for protein purification include affinity chromatography and a method involving the use of affinity resins and magnetic beads. Examples of a means for purification that has the site to which the first tag portion binds include a carrier having such site immobilized thereon and a column filled with such carrier. Examples of carriers include agarose and sepharose.

When a protein has a FLAG tag as the first tag portion, for example, a target protein to be immobilized, which has a FLAG tag as the first tag portion, is prepared via the aforementioned method. Subsequently, a solution containing the target protein to be immobilized is brought into contact with a carrier, such as agarose, carrying an anti-FLAG tag antibody. A complex of the target protein to be immobilized and the carrier, which have been bound via an antigen-antibody reaction, is then separated. For example, a FLAG peptide can then be added to the complex to competitively elute the target proteins to be immobilized. Further, the eluted target proteins to be immobilized can be separated from the carrier or the FLAG peptide via, for example, low-speed centrifugation (e.g., at 2,000 g).

In the method for immobilizing proteins according to the present invention, reactive groups on the carrier for immobilization 3 are then activated. The term "activation" refers to transition of the reactive groups so that they become capable of covalent binding with the target proteins to be immobilized, which are located in the vicinity thereof. If the carrier for immobilization 3 comprises carboxyl groups as reactive groups, for example, a mixed solution of N-ethyl-N'-(dimethylaminopropyl)carbodiimide (EDC) and N-hydroxysuccinimide (NHS) may be allowed to react therewith to activate the carboxyl groups.

In the method for immobilizing proteins according to the present invention, the target protein to be immobilized is allowed to react with the carrier for immobilization 3 to realize an interaction between the second tag portion of the target protein to be immobilized and the carrier for immobilization 3. The term "interaction" used herein refers to the binding of the second tag portion and the site to which the second tag portion binds, which results in the binding of the protein and the carrier for immobilization 3 at a relatively mild rate. In the case of a protein having a His tag as the second tag portion, for example, a metal such as nickel is trapped in NTA or IDA that has been introduced into the carrier for immobilization 3 to form a complex of the His tag with NTA or IDA via nickel. Nickel may be trapped in NTA or IDA before or after activation of the carrier for immobilization 3. Thus, a protein having a His tag can be subjected to interaction with the carrier for immobilization 3 into which NTA or IDA has been introduced.

When a protein has a GST tag as the second tag portion, a carrier for immobilization 3 into which glutathione has been introduced can be made to interact with the proteins by allowing them to be present together in a physiological phosphate buffer (e.g., PBS) or a physiological Hepes buffer (e.g., HBS). When proteins comprising antigenic peptides and a carrier for immobilization 3 into which antibodies have been introduced are used, they can also be made to interact with each other by allowing them to be present together in a physiological phosphate buffer (e.g., PBS) or a physiological Hepes buffer (e.g., HBS).

In the method for immobilizing proteins according to the present invention, the second tag portion of the target protein to be immobilized is allowed to interact with the carrier for immobilization 3 as mentioned above. Thus, the target proteins to be immobilized are located in the vicinity of the carrier for immobilization 3 at a relatively high density. This facilitates the covalent binding between the activated reactive groups and the proteins, and the covalent binding can easily take place between them.

When reactive groups are carboxyl groups, for example, the reactive groups covalently bind to amino groups that are present in the target proteins to be immobilized (i.e., amine coupling). When reactive groups are carboxyl groups, the carboxyl groups are modified with PDEA to form covalent bonds between free thiol groups in the target proteins to be immobilized and the reactive groups (i.e., ligand-thiol coupling). When the target proteins to be immobilized have carboxyl groups, such proteins are allowed to react with PDEA (2-(2-pyridinyldithio) ethaneamine hydrochloride) previously to modify the carboxyl groups with PDEA. The carboxyl groups on the carrier for immobilization 3 are first activated, the carboxyl groups are allowed to react with cystamine dihydrochloride, and the reaction product is then subjected to reduction with dithiothreitol (DTT) for conversion into thiol groups. Covalent bonds are formed between the PDEA-modified carboxyl groups and the thiol groups on the carrier for immobilization 3 (i.e., disulfide coupling). More specifically, surface thiol coupling takes place.

The target proteins to be immobilized are purified with the first tag portion, the second tag portion is allowed to interact with the site to which the second tag portion binds, and a covalent bond is formed between the reactive groups and the proteins. This enables immobilization of the target proteins to be immobilized on the carrier for immobilization. According to the method for immobilizing proteins of the present invention, the target proteins to be immobilized are purified with the first tag portion. Thus, biological materials containing contaminating proteins are removed, and the target proteins to be immobilized can be reacted in a dense concentration with the carrier for immobilization 3. In the method for immobilizing proteins of the present invention, the second tag portion is allowed to interact with the site to which the second tag portion binds. Thus, proteins can be present in a dense concentration in the vicinity of the carrier for immobilization 3. According to the method for immobilizing proteins of the present invention, therefore, very small amounts of target proteins to be immobilized can be located in a dense concentration in the vicinity of the carrier for immobilization 3 and can be covalently bound to the carrier for immobilization 3 without nonspecifically immobilizing contaminating proteins, which had been difficult via conventional techniques.

A sensor chip prepared via the method for immobilizing proteins according to the present invention can be applied to a system that detects an analyte having affinity to the immobilized proteins.

The term "analyte" refers to a substance having affinity to proteins that have been immobilized. Any known compound or novel compound may be an analyte. Examples thereof include nucleic acids, carbohydrates, lipids, proteins, peptides, amino acids, organic low-molecular weight compounds, a compound library prepared via combinatorial chemistry, a random peptide library prepared via solid-phase synthesis or phage display, and naturally occurring substances derived from microorganisms, plants and animals, or marine organisms.

As shown in FIG. 2, for example, an analyzer based on the principle of SPR comprises: a prism 4 located on the opposite principal surface relative to the principal surface of a substrate 1 on which a carrier for immobilization 3 is located; a light source 6 that permits a polarized light 5 to come into contact with the sensor chip through the prism 4; a detection unit 8 into which a reflected light 7 generated upon reflection of the polarized light 5 enters through the prism 4 via a metal membrane 2; and a flow cell 9 located in contact with the carrier for immobilization 3 having proteins immobilized thereon.

When the polarized light 5 is applied from the light source 6 to the metal membrane 2 in a manner such that the light is totally reflected, the intensity of the reflected light 7 is partially weakened, according to the principle of SPR. The angle at which a dark portion appears (i.e., a change in the refractive index) depends on the mass on the sensor chip. When the analyte is bound to the protein that has been immobilized on the carrier for immobilization 3, the mass changes (i.e., the mass increases), and the dark portion is shifted from I to II (FIG. 2). It is known that such shift takes place by 0.1 degree from I to II upon binding of 1 ng of substance per $mm^2$. If the mass decreases upon dissociation, however, the dark portion is shifted back by such degree from II to I.

The analyzer shown in FIG. 2 flushes a solution comprising a sample containing the analyte into the flow cell 9 and detects the amount of the darkened portion created by the reflected light 7 shifted from I to II with the detection unit 8. This analyzer displays, as the result of detection, changes in the mass on the sensor chip surface on the vertical axis and changes in the mass with the elapse of time as measured data (a sensorgram). The vertical axis is expressed in terms of resonance units (RU), and 1 RU is equivalent to 1 $pg/mm^2$. Such changes in the refractive index are substantially the same among all biomolecules (i.e., proteins, nucleic acids, and lipids), and interaction can be monitored in real time without labeling such biomolecules.

With the use of such SPR-based analyzer, interaction between a protein and an analyte can be analyzed, and a novel drug target or a novel candidate compound for a pharmaceutical preparation can be particularly effectively discovered. The sensor chip prepared via the method for immobilizing proteins according to the present invention can immobilize any proteins thereon regardless of the protein species. Also, such sensor chip can securely immobilize proteins for a long period of time. This enables screening of a novel drug target or a novel candidate compound for a pharmaceutical preparation using various species of proteins.

This description includes part or all of the contents as disclosed in the description and/or drawings of Japanese Patent Application No. 2003-307588, which is a priority document of the present application.

DESCRIPTION OF REFERENCE NUMERALS

Figure 1:
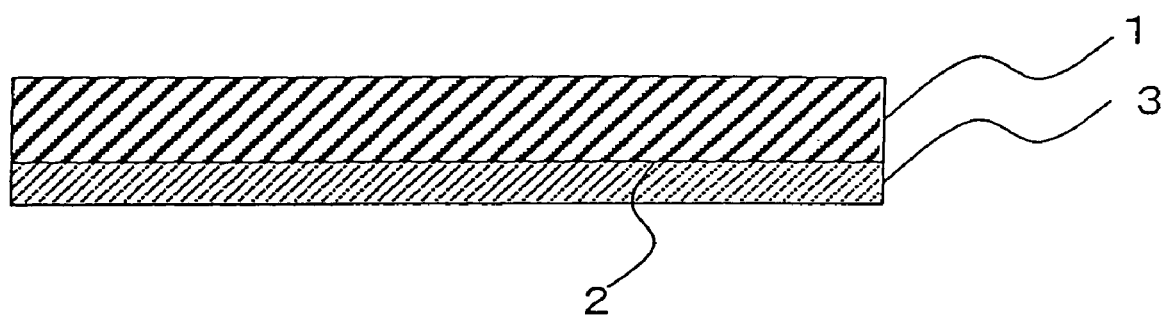
FIG. 1 shows a cross-section of an essential part of the sensor chip prepared via the method for immobilizing proteins according to the present invention.
Figure 2:
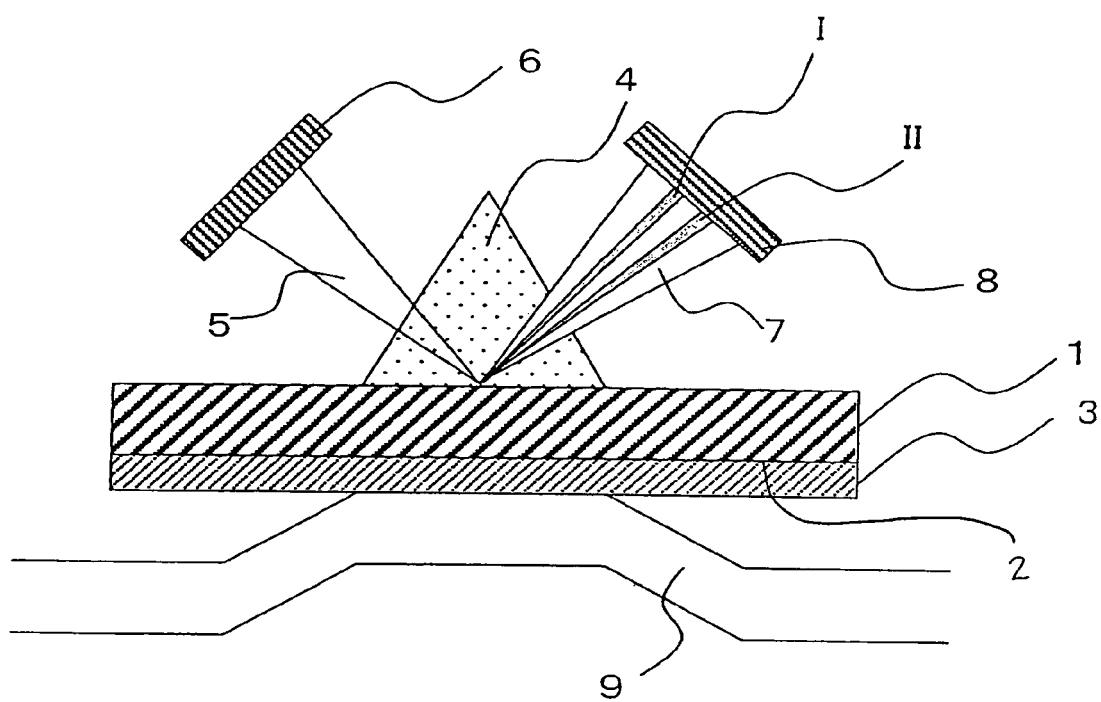
FIG. 2 schematically shows the construction of the analyzer based on the principle of SPR.

1: substrate; 2: metal membrane; 3: carrier for immobilization; 4: prism; 5: polarized light; 6: light source; 7: reflected light; 8: detection unit; and 9: flow cell

BEST MODE FOR CARRYING OUT THE INVENTION

EXAMPLES

Hereafter, the method for immobilizing proteins according to the present invention is described in greater detail with reference to the following examples, although the technical scope of the present invention is not limited thereto.

Comparative Example 1

As Comparative Example 1, a method for His tag purification of very small amounts of proteins expressed in a wheat germ cell-free system is described.

In this example, cyclophilin A (hereafter referred to as "Cyph") and FKBP12 (hereafter referred to as "FKBP") were employed as proteins. cDNAs of these proteins were subcloned into a pEU3-NII plasmid vector (Toyobo Co., Ltd.) for a wheat germ cell-free system via a genetic engineering technique to prepare a fusion protein in which the C terminus of the proteins were His-tagged. The nucleotide sequence and the amino acid sequence of the His tag (including a termination codon) are as shown below.

```
CAT CAC CAT CAC CAT CAC TAA        (SEQ ID NO: 1)

His His His His His His            (SEQ ID NO: 2)
```

Proteios (Toyobo Co., Ltd.) was employed as the wheat germ cell-free system.

Protein expression plasmids (5 μg each) for the wheat germ cell-free system constructed via a genetic engineering technique were employed as templates, and mRNA was synthesized at 37° C. for 4 hours in a 50-μl reaction system using thermo T7 RNA polymerase (Toyobo Co., Ltd.). Subsequently, the synthesized mRNA was then subjected to protein removal via phenol/chloroform treatment and was then buffer-exchanged with a buffer for Proteios via ethanol precipitation. In accordance with the protocol of the Proteios, proteins were synthesized at 26° C. for 20 hours using 10 μg of the synthesized mRNA in a 0.3-ml reaction system. As a control, a sample that had been subjected to the same reaction without the use of mRNA was prepared (a nonexpression control sample). The synthesized product (approximately 0.3 ml) was subjected to high-speed centrifugation (12,000 g for 10 minutes) to remove the precipitate, Tween 20 (BioRad) was added thereto to a concentration of 0.05%, and an aqueous solution of 1M imidazole was added thereto to a concentration of 10 mM. Ni-NTA Magnetic Agarose Beads (50 μl of 5% suspension, Qiagen) were added to the sample, they were mixed, and the resulting mixture was allowed to stand at room temperature for 1 hour. A magnet was applied to the mixture to separate the beads, and the separated beads were washed several times with 1 ml of buffer (e.g., PBS pH 7.4/0.05% Tween 20/20 mM imidazole). Subsequently, the recovered beads were mixed with 25 μl of elution buffer (e.g., PBS pH 7.4/0.05% Tween 20/250 mM imidazole), the resulting mixture was allowed to stand at room temperature for 5 to 10 minutes, a magnet was applied thereto to separate the beads, and the supernatant was recovered as an eluate (E1). The same procedure was repeated again to recover an eluate (E2).

Figure 3:
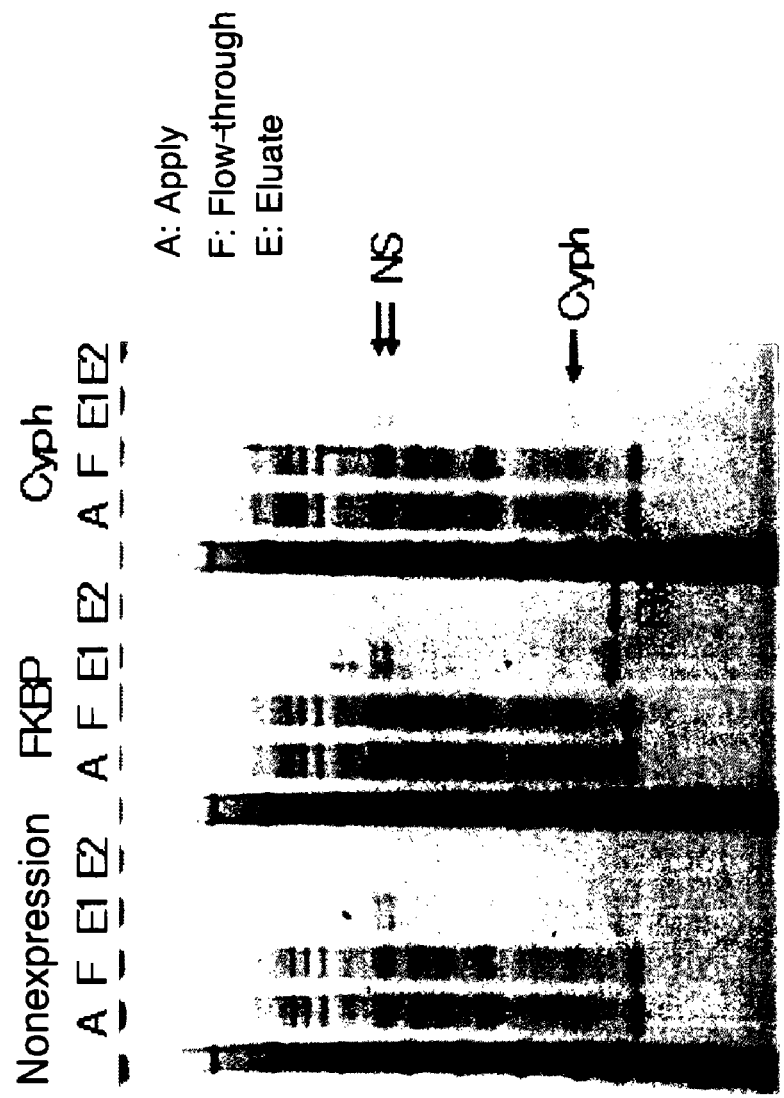
FIG. 3 is a photograph showing the results of analysis of proteins (cyclophilin A and FKBP12) purified with the use of a His tag via SDS-PAGE and via CBB staining.

The sample obtained via the aforementioned procedure was analyzed via SDS-PAGE and via CBB staining, and the results are shown in FIG. 3. In FIG. 3, lane A (Apply) represents a synthesis product of proteins before purification; lane F (Flow-through) represents a resultant after the separation and recovery of beads; and lane E1 and lane E2 each independently represent an eluate (E1) and an eluate (E2). The lanes to the left of each lane A represent a molecular weight marker. In the lane representing the FKBP or Cyph eluate (E1) sample, 2 bands were detected at around 50 kDa together with the target FKBP and Cyph proteins (arrows "NS" in FIG. 3). Since these bands were detected in nonexpression control samples, they were deduced to be the endogenous proteins of the wheat germ cell-free system, which have activities similar to a His tag.

Comparative Example 2

As Comparative Example 2, a method for concentrating very small amounts of proteins expressed in a wheat germ cell-free system on a sensor chip using a His tag (i.e., affinity concentration) without purification is described.

In the present example, Cyph and FKBP were employed as proteins. In the same manner as in Comparative Example 1, cDNAs of these proteins were subcloned into a pEU3-NII plasmid vector for the wheat germ cell-free system via a genetic engineering technique to prepare a fusion protein in which the C-terminus has been His-tagged. Proteios (Toyobo Co., Ltd.) was employed as the wheat germ cell-free system. The NTA sensor chip prepared by the present inventors was employed as a sensor chip. This NTA sensor chip comprises dextran provided on the substrate. The Biacore S51 (Biacore) was employed as an analyzer.

mRNAs and proteins were synthesized from each protein expression plasmid for the wheat germ cell-free system constructed via a genetic engineering technique in the same manner as in Comparative Example 1. As a control, the sample that had been subjected to the same reaction without the use of mRNA was prepared (a nonexpression sample). The synthesis product (approximately 0.3 ml) was subjected to high-speed centrifugation (12,000 g for 10 minutes) to remove the precipitate and then employed as a protein sample or a control sample for the following assay.

The CM5 sensor chip (Biacore) was washed with pure water and then treated with a mixed solution of 0.8M N-ethyl-N'-(dimethylaminopropyl)carbodiimide (EDC) and 0.27M N-hydroxysuccinimide (NHS) for 10 minutes. Subsequently, the sensor chip was treated with 16 mg/ml N-(5-amino-1-carboxypentyl)iminodiacetic acid, disodium salt, monohydrate (AB-NTA) for 2 hours. The sensor chip was washed with pure water and then with 50 mM NaOH and 50 mM HCl. Finally, the sensor chip was washed again with pure water, and the washed sensor chip was used as the NTA-sensor chip.

The NTA sensor chip was then set on the Biacore S51, and the system was filled with a running buffer (e.g., PBS pH 7.4/0.005% Tween20). Spot 1 was treated with 0.5M $NiCl_2$ at a flow rate of 10 µl/min for 1 minute (spot 2 was not treated), and $Ni^{2+}$ was allowed to bind selectively to the spot 1 of the NTA sensor chip. The protein sample or the control sample (a nonexpression sample) diluted 10-fold with a running buffer was flushed through the system (both spot 1 and spot 2) at a flow rate of 10 µl/min for 3 minutes.

Figure 4:
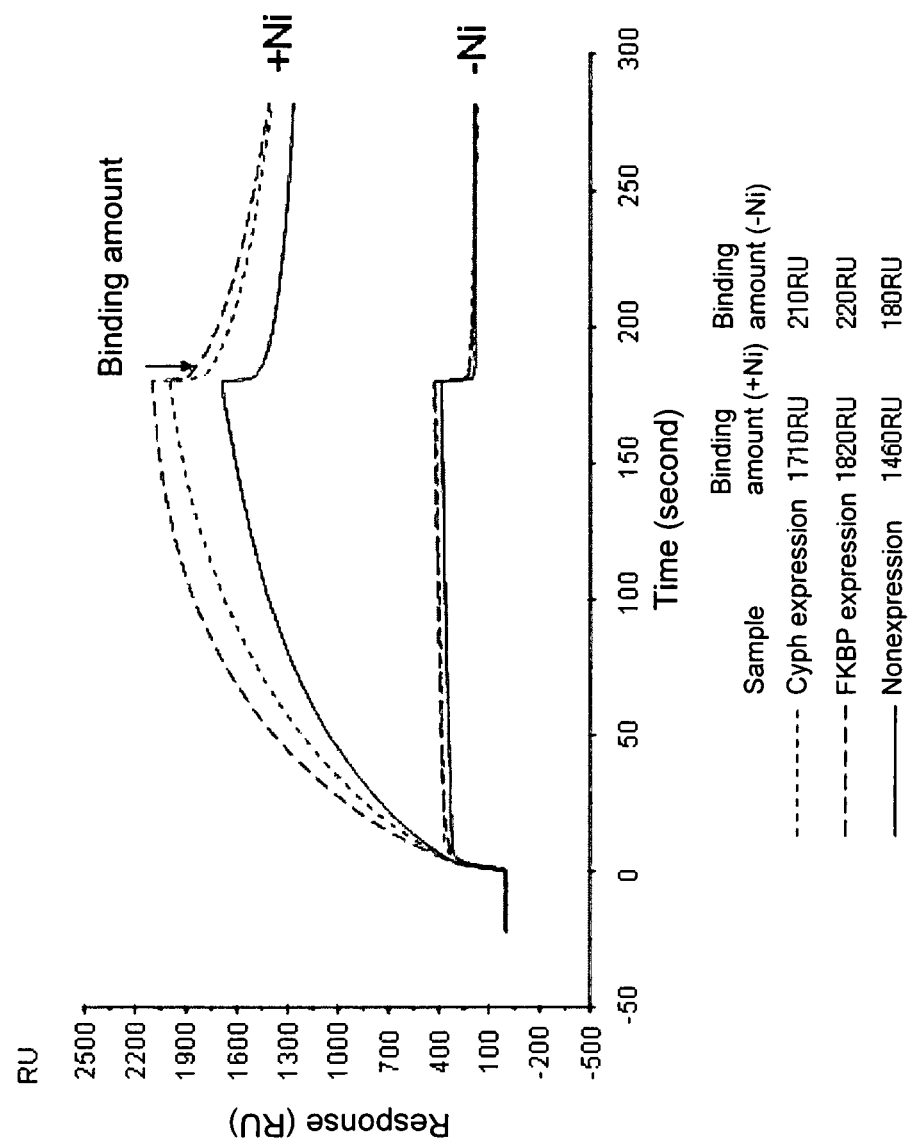
FIG. 4 shows a sensorgram generated when the unpurified proteins (cyclophilin A and FKBP12) are concentrated using a His tag on a sensor chip (affinity concentration).

FIG. 4 shows a sensorgram generated via the above procedure. On spot 1 (+Ni ion), approximately 1,700 RU Cyph proteins and approximately 1,800 RU FKBP proteins were bound to the sensor chip, and approximately 1,500 RU proteins in the control sample were also bound thereto.

When the proteins were concentrated without purification (i.e., affinity-concentrated), accordingly, contaminating proteins derived from the wheat-germ cell-free system were disadvantageously concentrated on a sensor chip, in addition to the target proteins. Also, the amounts of such contaminating proteins were deduced to be larger than those of the target proteins. On spot 2 (-Ni ion), the binding level was as low as approximately 200 RU in all the samples. Thus, it was considered that contaminating proteins were bound to the spot 1 of the sensor chip with the force of affinity to Ni ions, as with the case of the target proteins.

Example 1

As Example 1, a method for FLAG tag purification of very small amounts of proteins expressed in a wheat germ cell-free system is described.

In this example, Cyph was employed as a protein. cDNA of this protein was subcloned into a pEU3-NII plasmid vector for a wheat germ cell-free system via a genetic engineering technique to prepare a fusion protein in which the N terminus thereof was His- and FLAG-tagged. In this example, the FLAG tag refers to the first tag portion of the present invention. The nucleotide sequences and the amino acid sequences of the His tag and the FLAG tag (including initiation codons) are as shown below.

```
ATG CAT CAC CAT CAC CAT CAC GAC     (SEQ ID NO: 3)
TAC AAG GAC GAC GAT GAC AAA

Met His His His His His His Asp     (SEQ ID NO: 4)
Tyr Lys Asp Asp Asp Asp Lys
```

Proteios (Toyobo Co., Ltd.) was employed as the wheat germ cell-free system.

mRNAs and proteins were synthesized from 5 µg of expression plasmid for the wheat germ cell-free system constructed via a genetic engineering technique in the same manner as in Comparative Example 1. As a control, the sample that had been subjected to the same reaction without the use of mRNA was prepared (a nonexpression sample). The synthesis product (approximately 0.3 ml) was subjected to high-speed centrifugation (12,000 g for 10 minutes) to remove the precipitate, the resultant was mixed with 25 µl of M2 agarose (Sigma), and the resulting mixture was allowed to stand at room temperature for 1 hour. M2 agarose was separated and recovered from the mixture via low-speed centrifugation (2,000 g for 3 minutes) and washed several times with 1 ml of buffer (e.g., PBS pH 7.4/0.1% Tween 20). The recovered M2 agarose was mixed with 50 µl of 0.1 mg/ml FLAG peptide (Sigma), and the resulting mixture was allowed to stand at room temperature for 1 hour. The supernatant separated from the mixture via low-speed centrifugation was recovered as an eluate (E1). The same procedure was repeated to recover an eluate (E2).

Figure 5:
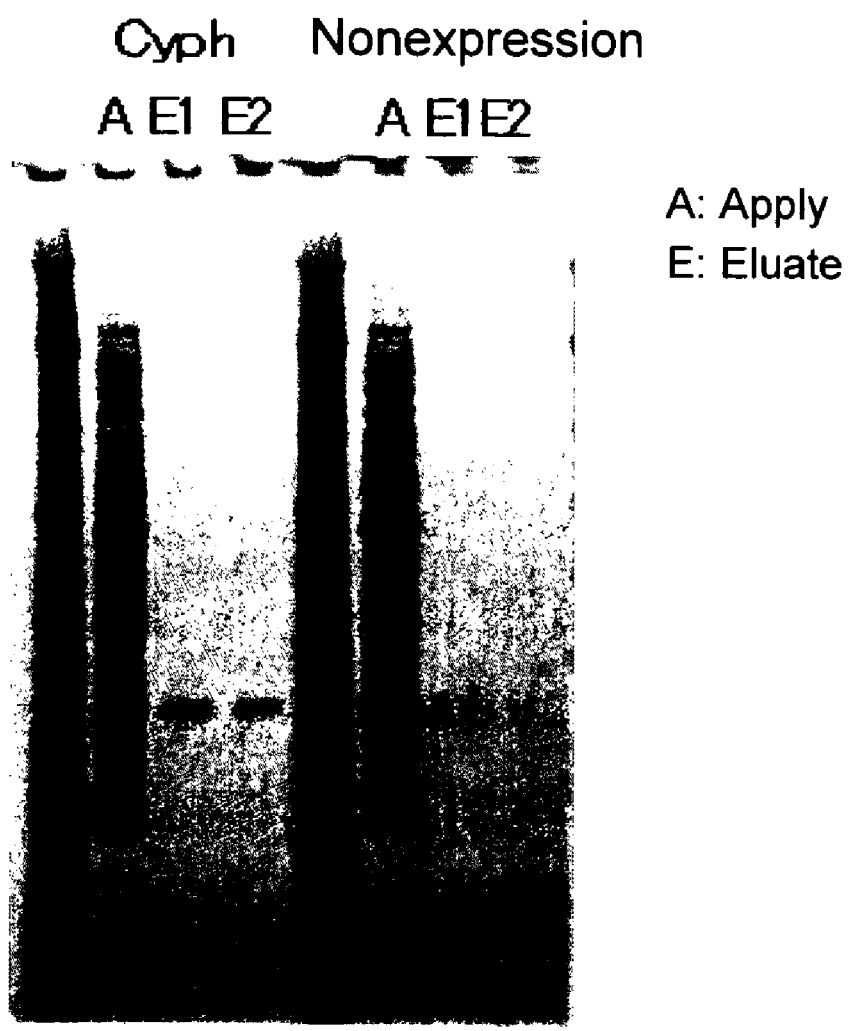
FIG. 5 is a photograph showing the results of analysis of the FLAG tag-purified proteins (cyclophilin A) via SDS-PAGE and via CBB staining.

The sample obtained via the aforementioned procedure was analyzed via SDS-PAGE and via CBB staining, and the results are shown in FIG. 5. In FIG. 5, lane A (Apply) represents a synthesis product of proteins before purification; and lane E1 and lane E2 each independently represent an eluate (E1) and an eluate (E2). The lanes to the left of each lane A represent a molecular weight marker. As is apparent from FIG. 5, only the target protein Cyph was detected in the lanes representing eluates (E1 and E2), and no problematic contaminating protein was detected.

Example 2

As Example 2, a method for concentrating proteins on a sensor chip with the use of a His tag (affinity concentration) following FLAG tag purification of very small amounts of proteins expressed in the wheat germ cell-free system according to the present invention is described.

In this example, Cyph was employed as a protein. In the same manner as in Example 1, cDNA of this protein was subcloned into a pEU3-NII plasmid vector for a wheat germ cell-free system via a genetic engineering technique to prepare a fusion protein in which the N terminus thereof was His- and FLAG-tagged. The term "FLAG tag" refers to the first tag portion and the term "His tag" refers to the second tag portion in the present invention. Proteios (Toyobo Co., Ltd.) was employed as the wheat germ cell-free system. The NTA sensor chip (a Biacore chip, Biacore) was employed as a sensor chip. This NTA sensor chip comprises dextran provided on the substrate. The Biacore 3000 (Biacore) was employed as an analyzer.

mRNAs and proteins were synthesized from 5 µg of expression plasmid for the wheat germ cell-free system constructed via a genetic engineering technique in the same manner as in Comparative Example 1. As a control, the sample that had been subjected to the same reaction without the use of mRNA was prepared (a nonexpression sample). The synthesis product (approximately 0.3 ml) was subjected to high-speed centrifugation (12,000 g for 10 minutes) to remove the precipitate, the resultant was mixed with 25 µl of M2 agarose (Sigma), and the resulting mixture was allowed to stand at room temperature for 1 hour. M2 agarose was separated and recovered from the mixture via low-speed centrifugation (2,000 g for 3 minutes) and washed several times with 1 ml of buffer (e.g., PBS pH 7.4/0.1% Tween 20). The recovered M2 agarose was mixed with 75 µl of 0.1 mg/ml FLAG peptide (Sigma), and the resulting mixture was allowed to stand at room temperature for 1 hour. The supernatant separated from the mixture via low-speed centrifugation was recovered as an eluate. An eluate recovered from the sample synthesized with the use of mRNA was employed as a protein sample, and an eluate recovered from the nonexpression sample was employed as a control sample below.

The NTA sensor chip was then set on the Biacore 3000, and the system was filled with a running buffer (e.g., PBS pH 7.4/0.005% Tween 20). Subsequently, the system was treated with 0.5M $NiCl_2$ at a flow rate of 10 µl/min for 1 minute, and $Ni^{2+}$ was allowed to bind to the NTA sensor chip. The protein sample or the control sample was then flushed through the system at a flow rate of 10 µl/min for 1 minute.

Figure 6:
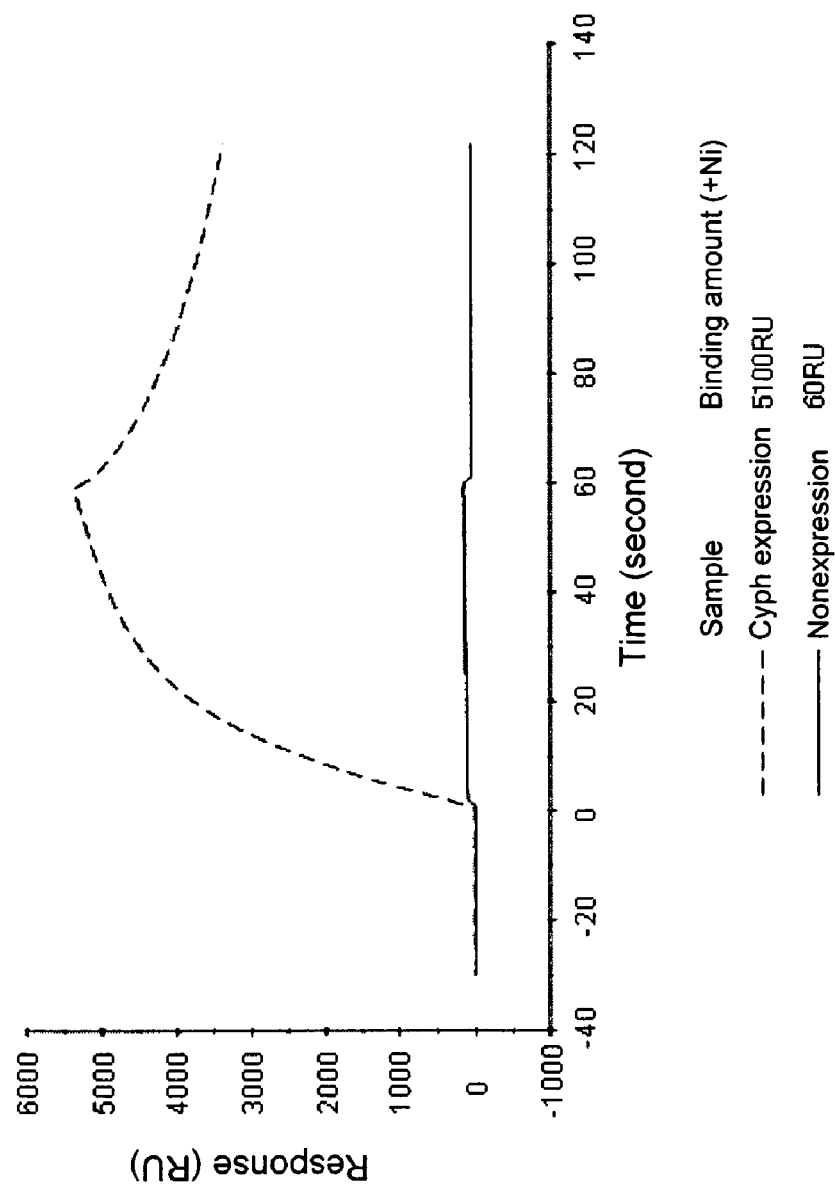
FIG. 6 shows a sensorgram generated when FLAG tag-purified proteins (cyclophilin A) are concentrated on a sensor chip with the use of a His tag (affinity concentration).

FIG. 6 shows a sensorgram generated via the above procedure. Approximately 5,100 RU of the protein in the protein sample was bound to the sensor chip, and approximately 60 RU of the protein in the control sample was only bound thereto. This indicates that only the target Cyph protein could be effectively concentrated on the sensor chip via the previous process of protein purification with a FLAG tag.

Example 3

As Example 3, a method for FLAG tag-purifying very small amounts of proteins expressed in the wheat germ cell-free system via the method of the present invention and then immobilizing the purified proteins on the sensor chip via covalent biding (amine coupling) and with the use of a His tag is described.

In this example, Cyph was employed as a protein. In the same manner as in Example 1, cDNA of this protein was subcloned into a pEU3-NII plasmid vector for a wheat germ cell-free system via a genetic engineering technique to prepare a fusion protein in which the N terminus thereof was His- and FLAG-tagged. The term "FLAG tag" refers to the first tag portion and the term "His tag" refers to the second tag portion in the present invention. Proteios (Toyobo Co., Ltd.) was used as the wheat germ cell-free system. The NTA sensor chip (a Biacore chip, Biacore) used in Example 2 was employed as a sensor chip. The Biacore 3000 (Biacore) was employed as an analyzer.

In the same manner as in Example 2, mRNA and proteins were synthesized, and eluates were recovered. An eluate recovered from the sample synthesized with the use of mRNA was employed as a protein sample for immobilization, and an eluate recovered from the nonexpression sample was employed as a control sample for immobilization.

The NTA sensor chip was then set on the Biacore 3000, and the system was filled with a running buffer (e.g., PBS pH 7.4/0.005% Tween 20). Subsequently, the system was treated with 0.5M $NiCl_2$ at a flow rate of 10 µl/min for 1 minute, and $Ni^{2+}$ was allowed to bind to the NTA sensor chip. Further, a mixed solution of 0.2M N-ethyl-N'-(dimethylaminopropyl) carbodiimide (EDC) and 0.05M N-hydroxysuccinimide (NHS) was flushed through the system at a flow rate of 10 µl/min for 7 minutes to activate carboxyl groups on the NTA sensor chip (i.e., formation of active intermediates). The protein or control sample for immobilization diluted 5-fold with a running buffer was then flushed through the system at a flow rate of 10 µl/min for 10 minutes. Thus, the target proteins were concentrated on the sensor chip via the effects of a His tag, and the proteins were also allowed to chemically react with the active intermediates with the aid of amino groups for covalent binding, thereby immobilizing the proteins on the sensor chip. Subsequently, a 1M ethanolamine buffer was flushed through the system at a flow rate of 10 µl/min for 7 minutes to decompose the unreacted active intermediates. Thus, immobilization was terminated. Further, a 250 mM imidazole buffer was flushed through the system at a flow rate of 10 µl/min for 1 minute to remove the unreacted proteins from the sensor chip surface.

Figure 7:
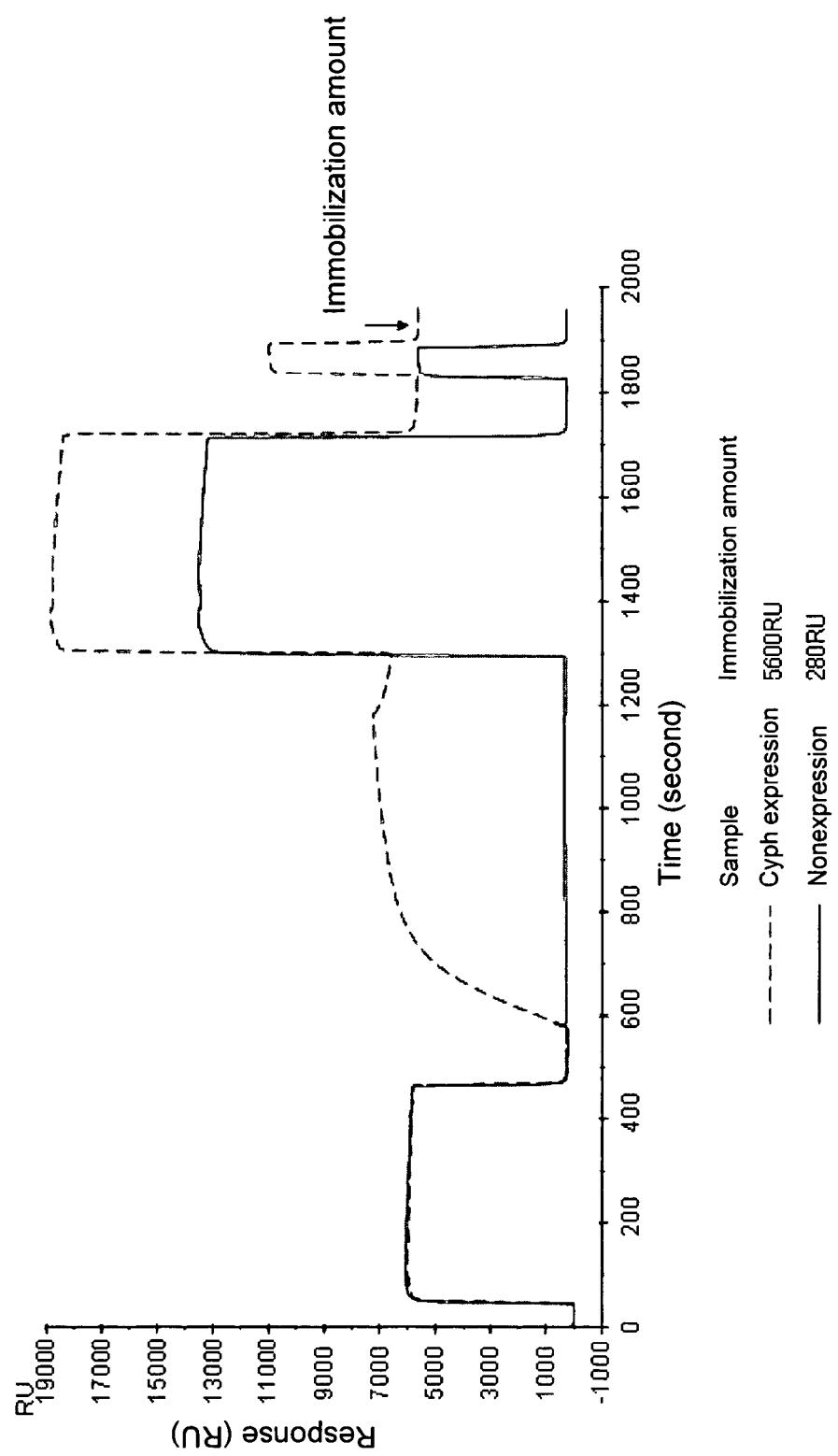
FIG. 7 shows a sensorgram generated by the purification of proteins (cyclophilin A) with a FLAG tag and the immobilization of the purified proteins via covalent binding (amine coupling) and with the use of a His tag on a sensor chip.

FIG. 7 shows a sensorgram generated via the above procedure. Approximately 5,600 RU of the protein in the protein sample for immobilization was bound to the sensor chip, and approximately 280 RU of the protein in the control sample for immobilization was only bound thereto. This indicates that only the target Cyph protein was effectively immobilized on the sensor chip.

Example 4

As Example 4, a method for immobilizing proteins, which is carried out in the same manner as in Example 3 except for the use of PPARγ and RAR-α as proteins, is described.

In this example, a Biacore S51 (Biacore) was used as an analyzer, and the NTA sensor chip used in Comparative Example 2 was used as a sensor chip. When injecting the protein sample for immobilization, the sample was not diluted with a running buffer, and the injection time was for 15 minutes.

Figure 8:
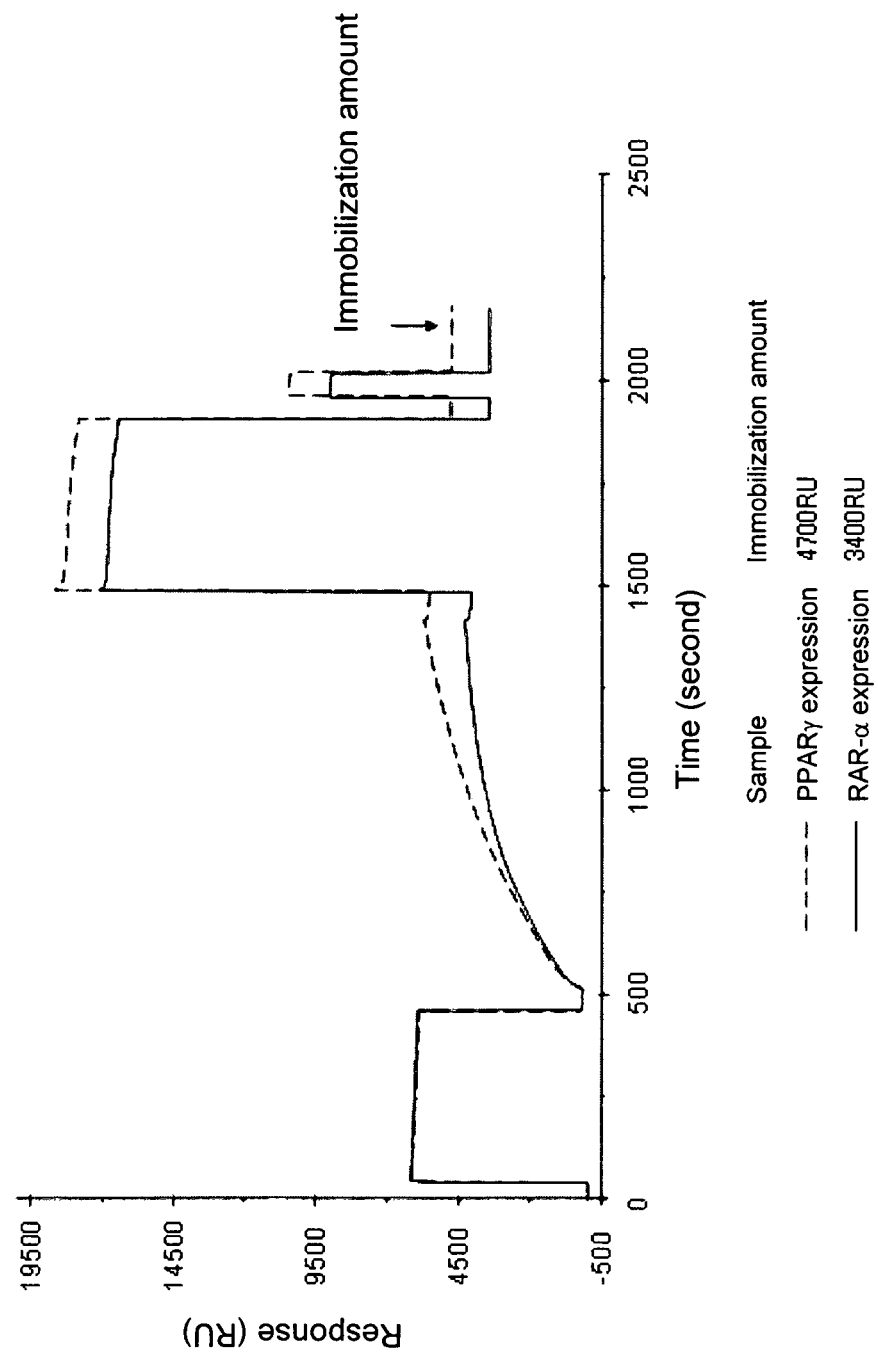
FIG. 8 shows a sensorgram generated by the purification of proteins (PPARγ and RAR-α) with a FLAG tag and the immobilization of the purified proteins via covalent binding (amine coupling) and with the use of a His tag on a sensor chip.

FIG. 8 shows a sensorgram generated via the above procedure. Approximately 4,700 RU of the PPARγ proteins were immobilized. Approximately 3,400 RU of the RAR-α proteins were immobilized. This suggests that the method for immobilizing proteins of the present invention can be applied to any protein species.

Example 5

As Example 5, a method for assaying the protein-analyte interaction using proteins expressed in the wheat germ cell-free system and immobilized on the sensor chip according to the method of the present invention is described.

Cyph and FKBP were employed as proteins. Cyclosporin A known to bind to Cyph and FK506 known to bind to FKBP were used as the analytes. A Biacore S51 (Biacore) was used as an analyzer, and the NTA sensor chip used in Comparative Example 2 was used as a sensor chip. Proteins were immobilized on the sensor chip in the same manner as in Example 3. As a result, approximately 2,000 RU of the FKBP proteins were immobilized on spot 1 of the same flow cell, and approximately 3,400 RU of the Cyph proteins were immobilized on spot 2 thereof.

Figure 9:
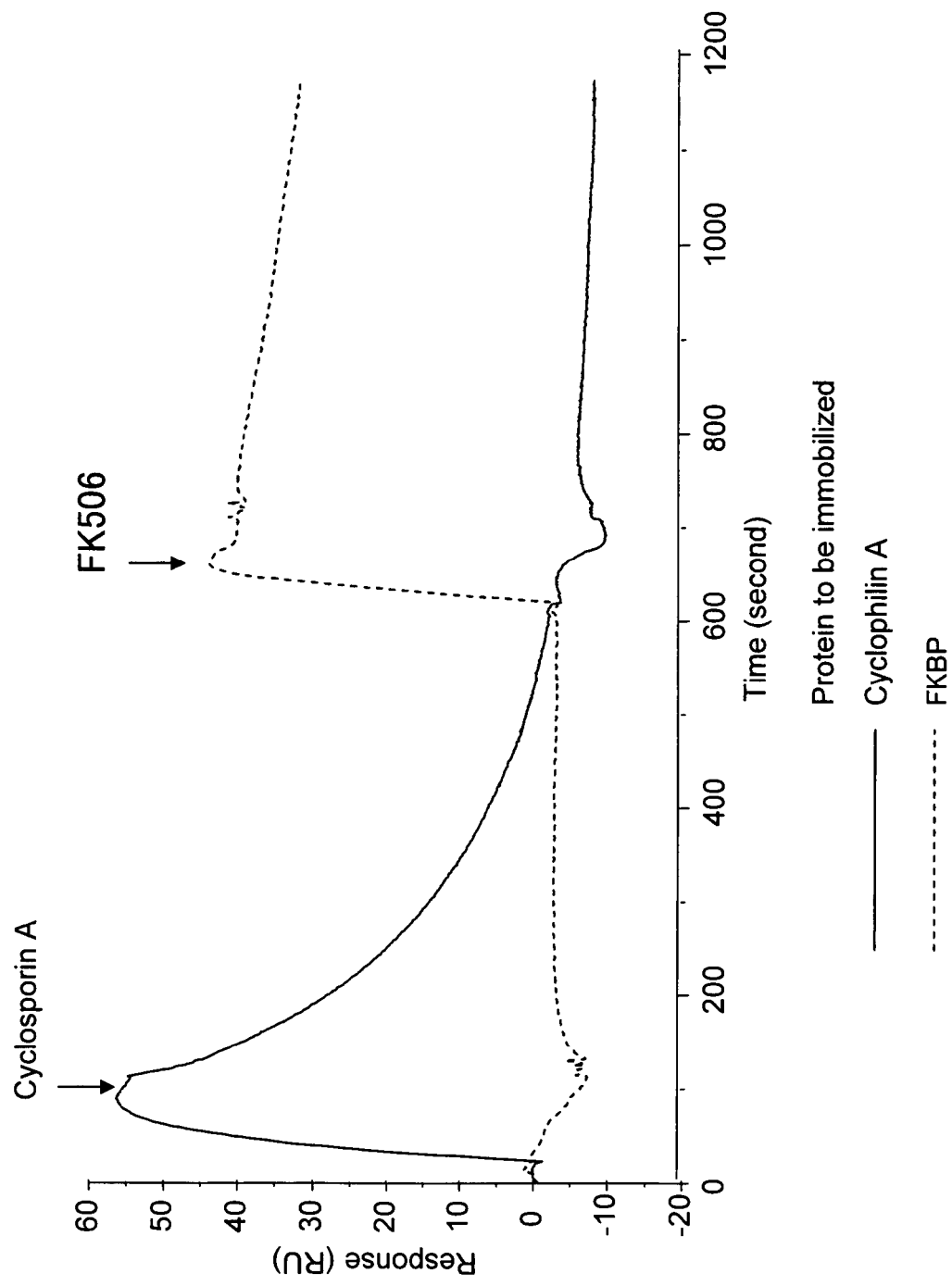
FIG. 9 shows the results of an assay of the binding between cyclosporin A and cyclophilin A immobilized via the method for immobilizing proteins according to the present invention and the binding between immobilized FKBP12 and FK506.

Cyclosporin A (1 uM) was injected over the sensor chip for 1.5 minutes, the sensor chip was allowed to stand for approximately 8 minutes until the response returned back to the baseline level, and 1 uM FK506 was injected thereto for 1.5 minutes. FIG. 9 shows the sensorgram generated via the above procedure. When cyclosporin A was injected, a response of approximately 43 RU was detected only at the Cyph spot. When FK506 was injected, a response of approximately 51 RU was detected only at the FKBP spot.

As is apparent from the above, the method of the present invention enables the detection of the specific protein-analyte interaction.

All publications, patents, and patent applications cited herein are incorporated herein by reference in their entirety.

INDUSTRIAL APPLICABILITY

In the method for immobilizing proteins of the present invention, a target protein to be immobilized, which has the first tag portion and the second tag portion, is purified with the first tag portion, the reactive group on the carrier for immobilization is activated, and the second tag portion of the protein is then allowed to interact with and covalently bind to the carrier. According to the method for immobilizing proteins of the present invention, various species of proteins can be securely immobilized on a carrier for immobilization, regardless of the amounts of the target proteins and without nonspecifically immobilizing contaminating proteins.

Sequence Listing Free Text

SEQ ID NOs: 1 and 2 each independently show the nucleotide sequence and the amino acid sequence of a His tag (including a termination codon).

SEQ ID NOs: 3 and 4 each independently show the nucleotide sequence and the amino acid sequence of a His tag and a FLAG tag (including initiation codons).

What is claimed is:

1. A method for immobilizing fusion proteins comprising: step 1 of purifying target proteins to be immobilized, which have a first tag portion and a second tag portion by separating and extracting the fusion protein via purification means having the site to which the first tag portion binds; step 2 of activating reactive groups capable of covalently binding to the fusion proteins on a carrier for immobilization, wherein the carrier has the site to which the second tag portion binds; and step 3 of allowing a solution containing the proteins purified in step 1 to react with the carrier after step 2, wherein, in step 3, the fusion proteins are immobilized on the carrier by covalent binding reaction between the reactive groups and the fusion proteins while being concentrated on the carrier by interactions between the second tag portion and the site of the carrier to which the second tag portion binds.

2. The method for immobilizing proteins according to claim 1, wherein the site to which the first tag portion binds is an antibody that reacts with the first tag portion.

3. The method for immobilizing proteins according to claim 2, wherein the first tag portion is a FLAG tag, and the site to which the first tag portion binds is an anti-FLAG tag antibody.

4. The method for immobilizing proteins according to claim 1, wherein the reactive groups are carboxyl groups and step 3 comprises subjecting the carboxyl groups to amine coupling with amino groups of the target proteins to be immobilized.

5. The method for immobilizing proteins according to claim 1, wherein the second tag portion is a histidine tag, and step 3 comprises subjecting the histidine tag to interaction with the carrier.

6. The method for immobilizing proteins according to claim 5, wherein step 3 comprises subjecting the histidine tag to a chelate-mediated interaction with the carrier.

7. The method for immobilizing proteins according to claim 6, wherein step 3 comprises subjecting the histidine tag to an $Ni^{2+}$-nitrilotriacetic acid (Ni-NTA)-mediated interaction with the carrier.

8. The method for immobilizing proteins according to claim 6, wherein step 3 comprises subjecting the histidine tag to an $Ni^{2+}$-iminodiacetic acid (Ni-IDA)-mediated interaction with the carrier.

9. The method for immobilizing proteins according to claim 1, wherein the site of the carrier to which the second tag portion binds is an antibody that reacts with the second tag portion.

10. The method for immobilizing proteins according to claim 9, wherein the second tag portion is a histidine tag, the antibody is an anti-histidine tag antibody, and step 3 comprises subjecting the histidine tag to the anti-histidine tag antibody-mediated interaction with the carrier.

11. The method for immobilizing fusion proteins according to claim 1, wherein the fusion proteins are prepared by use of a recombinant vector comprising the first tag portion-encoding gene and the second tag portion-encoding gene in frame with a target protein-encoding gene.

* * * * *